United States Patent [19]
Nakanishi

[11] Patent Number: 5,815,258
[45] Date of Patent: Sep. 29, 1998

[54] LIQUID SAMPLE CELL FOR AN OPTICAL MEASUREMENT APPARATUS

[75] Inventor: Hiroaki Nakanishi, Nara, Japan

[73] Assignee: Shimadzu Corporation, Kyoto, Japan

[21] Appl. No.: 800,386

[22] Filed: Feb. 14, 1997

[30] Foreign Application Priority Data

Feb. 15, 1996 [JP] Japan .................................. 8-027795

[51] Int. Cl.[6] .................................................. G01N 21/05
[52] U.S. Cl. ............................................ 356/246; 250/576
[58] Field of Search ................................ 386/246, 39–42, 386/336–343; 356/72, 73, 440; 250/576

[56] References Cited

U.S. PATENT DOCUMENTS

| | | | |
|---|---|---|---|
| 4,823,168 | 4/1989 | Kamahori et al. | ....................... 356/246 |
| 5,273,633 | 12/1993 | Wang . | |
| 5,608,517 | 3/1997 | Munk | ....................... 356/246 |

FOREIGN PATENT DOCUMENTS

A-0-488-947 6/1992 European Pat. Off. .

OTHER PUBLICATIONS

E. Verpoorte et al.; Sensors and Actuators B, "A silicon flow cell for optical detection in miniaturized total chemical analysis systems", vol. B6, No. 1–3, pp. 66–70, (1992).
DeGrandpe, M.D. et al.; Analytical Chemistry, "Thin Film Planar Waveguide Sensor for Liquid Phase Absorbance Measurements", vol. 62, No. 18, pp. 2012–2017, (1990).
Tsunoda, Kin–Ichi et al.; Applied Spectroscopy, "The Possibility of Signal Enhancement in Liquid Absorption Spectrometry With A Long Capillary Cell Utilizing Successive Total Reflection At The Outer Cell Surface", vol. 43, No. 1, pp. 49–55, (1989).
H. Swerdlow et al., "Three DNA Sequencing Methods Using Capillary Gel Electrophoresis and Laser–Induced Fluorescence", Anal. Chem., 1991, 63, 2835–2841.

*Primary Examiner*—Frank G. Font
*Assistant Examiner*—Amanda Merlino
*Attorney, Agent, or Firm*—Oliff & Berridge PLC

[57] ABSTRACT

A liquid sample cell used in an optical measurement apparatus in which a liquid sample flows through a flow path of the sample cell while a measurement light travels through the liquid sample in the flow path. The liquid sample cell is composed of: a first glass plate and a second glass plate fixed to each other; a groove for constituting the flow path formed in the first glass plate by a photolithographic method; reflection layers formed on the internal surface of the groove and on the internal surface of the other glass plate; and an entrance window and an exit window formed in the reflection layers to let the measurement light into the flow path and to let the measurement light out from the flow path. The measurement light is reflected by the reflection layers many times in the flow path. Since the measurement light travels a long distance in the liquid sample, the sensitivity of the optical measurement is improved, while the capacity of the flow path is minimized preventing diffusion or mixture of components separated by a chromatographic column, for example.

17 Claims, 4 Drawing Sheets

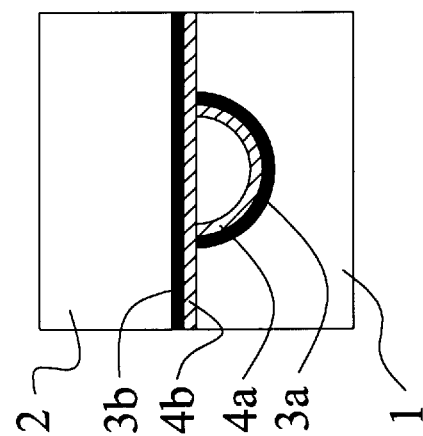
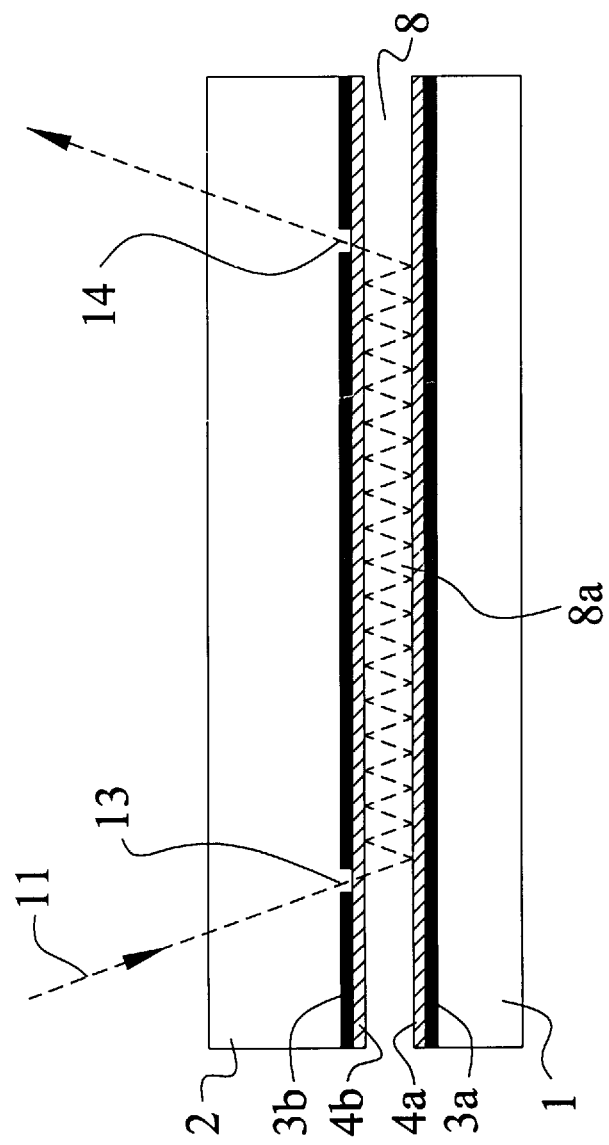
Fig. 1B
Fig. 1A

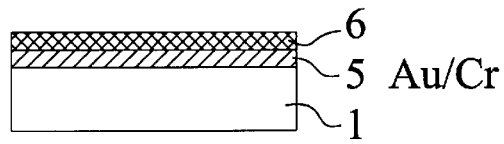
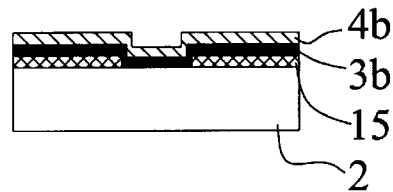
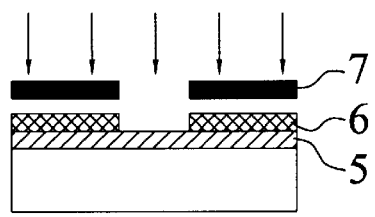
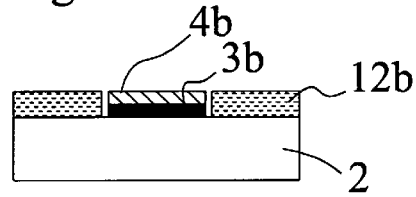
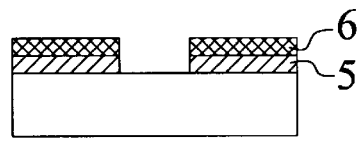
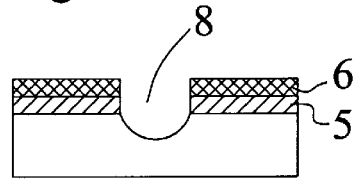
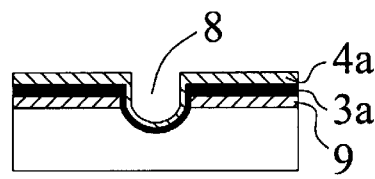
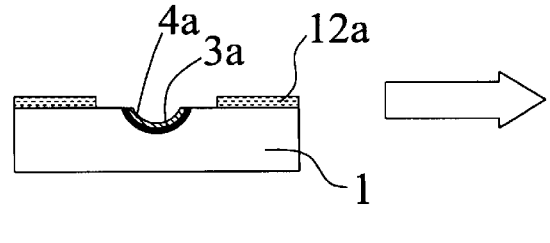
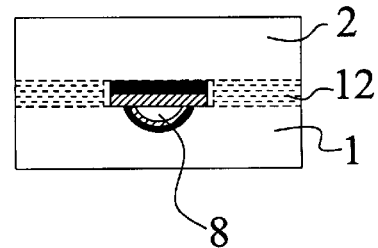

A: He-Ne LASER ( λ=543.5nm)   B: LENS   C: CAPILLARY
D: CELL    E: OBJECT LENS    F: PINHOLE   G: FILTER
H: PHOTO-MULTIPLIER    I: COMPUTER

LIQUID SAMPLE CELL FOR AN OPTICAL MEASUREMENT APPARATUS

The present invention relates to a liquid sample cell and an optical measurement apparatus using the liquid sample cell. Optical measurement apparatuses are widely used in various analyzers, such as capillary electrophoresis, liquid chromatographs and flow injection analyzers, for measuring a very small amount of component or components in a liquid sample precisely and swiftly. Such analyzers are utilized in such fields as an environmental analysis, clinical medicine, pharmaceutics, etc.

BACKGROUND OF THE INVENTION

In the optical measurement apparatus, a liquid sample flows through the liquid sample cell, while a measurement light (visible light and ultraviolet light are usually used) is let pass through the liquid sample. The amount of light absorbed by the liquid sample or emitted from the liquid sample is measured, usually with respect to the wavelength, whereby a component or components included in the liquid sample is identified.

A liquid sample cell normally has an inlet, a flow path and an outlet. The inlet of the liquid sample cell is connected to an outlet of a column of a chromatograph or a separator of an analyzer. The flow path includes a measurement space, and an entrance window and an exit window are provided for the measurement space. Measurement light generated by a light source comes into the measurement space through the entrance window, travels through the liquid sample in the measurement space where the measurement light interacts with the liquid sample, and goes out from the exit window. The measurement light is then measured by a light detector of the optical measurement apparatus.

A disadvantage of a conventional liquid sample cell is its relatively large capacity. The capacity of a liquid sample cell of a capillary electrophoresis, for example, is large compared to that of the glass capillary for separating the components of a liquid sample, so that components of a small amount once separated and concentrated by the glass capillary diffuse in the solvent again or are mixed again.

Some efforts have been made to reduce the capacity of the liquid sample cell. One is shown in "Analytical Chemistry", Vol.63 (1991), p.2835, as in FIG. 7, where a liquid sample cell having a reduced capacity of the measurement space is used in a laser excited fluorescent detector. But the capacity of the cell is not yet so small as to obtain a desired high resolution and precision of the measurement. Another approach to the reduced capacity is to use a part of the capillary column itself as the liquid sample cell. While the capacity of the measurement space is quite small in this case, it has a serious drawback that the travel distance of the measurement light in the liquid sample is also very small. This much deteriorates the sensitivity of the measurement.

SUMMARY OF THE INVENTION

An object of the present invention is therefore to provide a liquid sample cell which has a measurement space of a very small capacity and still is able to provide a large travel distance of the measurement light. Another object of the present invention is to provide an optical measurement apparatus designed to adapt to such a liquid sample cell.

In a liquid sample cell used for an optical measurement apparatus, a liquid sample flows through a flow path of the sample cell while a measurement light travels through the liquid sample in the flow path. According to the present invention, the liquid sample cell includes:

a first glass plate and a second glass plate fixed to each other;

a groove formed in at least one of the first glass plate and the second glass plate, where the groove constitutes the flow path;

reflection layers formed on the internal surface of the groove and on the internal surface of the other glass plate; and an entrance window and an exit window formed in the reflection layers to let the measurement light into the flow path and to let the measurement light out from the flow path after the measurement light is reflected by the reflection layers a plurality of times in the flow path.

Instead of on the internal surfaces, the reflection layers may be formed on the external surfaces of the glass plates.

The cross-sectional area of the flow path is preferably about the same as that of the capillary column for separating components of the liquid sample.

The groove is most preferably formed by a photolithographic (or photofabrication) method to minimize the capacity of the flow path. Other micro-machining methods may be used of course if the capacity of the flow path is also minimized.

When the reflection layers are formed on the external surfaces, the material of the glass plates should be chosen to have a large transmittance to the measurement light used. For an ultraviolet light, UV-22 of Hoya Corp. and #9741 of Corning Corp. are recommended. Further clarity to the ultraviolet light is obtained by quartz glass. The thickness of the glass plates should also be minimized (preferably from several hundred micrometers to 1 mm) to prevent attenuation of the measurement light while it is reflected a plurality of times between the reflection layers. The size of the measurement space is preferred to be less than several hundred micrometers to prevent deterioration of the resolution. When the reflection layers are formed on the internal surfaces, the thickness of at least one of the glass plate that allows the measurement light to pass through the entrance and exit windows should be minimized and its material should be adequately chosen for the same reason.

For the reflection layers, aluminum is one of the recommended materials which has a relatively large reflection efficiency to the ultraviolet light. When the reflection layers are formed on the inner surface of the flow path, it is preferable to cover the reflection layers with protection layers of, for example, quartz with tens to hundreds of nanometer thickness to prevent the reflection layers from being attacked by the liquid sample.

Since, as described above, the capacity of the flow path can be minimized in the present invention, the possibility of diffusion or mixture of the components once separated by a capillary column, for example, is greatly reduced. Further, since the measurement light travels a long distance in the liquid sample while being reflected by the reflection layers many times, the sensitivity of the optical measurement is improved.

Other features and modifications to the above liquid sample cell, and an optical measurement apparatus using such a liquid sample cell are fully described in the detailed description of the preferred embodiments that follows.

BRIEF DESCRIPTION OF THE DRAWINGS

FIGS. 1A and 1B are longitudinal and transverse cross-sectional views of a liquid sample cell as the first embodiment of the present invention.

FIGS. 2A to 2I illustrate the process for producing the liquid sample cell of the first embodiment.

DETAILED DESCRIPTION OF PREFERRED EMBODIMENTS

Figure 3:
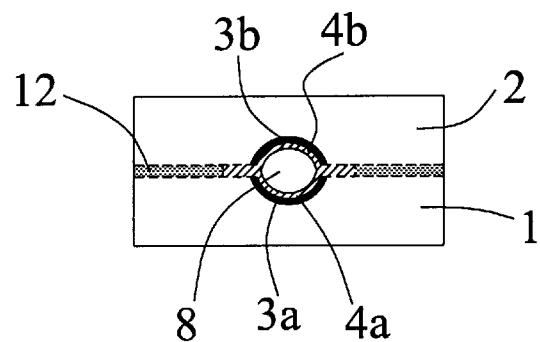
FIG. 3 is a transverse cross-sectional view of another liquid sample cell embodying the present invention which has an oval cross-section of the flow path.

The first embodiment of the present invention is now described with reference to the attached drawings. FIGS. 1A and 1B show a longitudinal and transverse cross-sectional view of a liquid sample cell according to the present invention, in which numerals 1 and 2 denote glass plates. The glass plates 1 and 2 are made of quartz, for example. On one face of one of the glass plates 1 is formed a groove for a flow path 8 having width and depth of less than several hundred micrometers. A reflection layer 3a is formed on the internal surface of the groove, and a protection layer 4a is formed on the reflection layer 3a. The reflection layer 3a may be formed on the entire internal surface of the groove, or it may be formed on a part of the internal surface that reflects the measurement light. The reflection layer 3a is made of aluminum, for example, with the thickness of up to several hundred nanometers, and the protection layer 4a is made of a sputtered quartz with the thickness of several tens to hundreds of nanometers.

On the opposing face of the other glass plate 2 is formed a second reflection layer 3b corresponding to the first reflection layer 3a, and a second protection layer 4b is also formed on the second reflection layer 3b. As will be detailed later with reference to FIGS. 2F and 2H, thin layers 12a and 12b of low melting point glass, formed by sputtering for example, having thickness of several hundred nanometers are formed on the opposing faces (internal surfaces) of the two glass plates 1 and 2. When the two glass plates 1 and 2 are attached to each other with the low melting point glass layers 12a and 12b in contact, and they are heated until the low melting point glass layers 12a and 12b fuse, the air-tight flow path 8 is formed.

In measurement, a part of the flow path 8 of the liquid sample cell is used as a measurement space 8a. Thus, in the present embodiment, the measurement space 8a renders a sufficiently small capacity. The optical system can be arranged so that an incident light 11 enters the measurement space 8a through an entrance window 13 and goes out through an exit window 14 after reflecting several times between the opposing reflection layers 3a and 3b of the flow path 8. By increasing the frequency of the reflection in the measurement space 8a, the travel distance of the measurement light 11 increases and the measurement light 11 interacts more with the measuring object, i.e., the liquid sample, in the measurement space 8a, which renders a higher measurement sensitivity.

The manufacturing process of the above liquid sample cell is then described with reference to FIGS. 2A–2I. After the first glass plate 1 is cleaned, as shown in FIG. 2A, an etching protection layer 5 is formed by a vacuum vapor deposition. An example of the etching protection layer 5 is a double layer of gold (Au) of about 200 nanometer thickness and chromium (Cr) of about 20 nanometer thickness. On the etching protection layer 5 is formed a photo-resist layer 6 for patterning the etching protection layer 5. AZ4620 (trade name by Hoechst Industry) can be used as the photo-resist, in which case, for example, the photo-resist agent is spin-coated on the etching protection layer at 3000 rpm for 40 seconds producing a 7 micrometer thickness. It is a matter of course that the name of the photo-resist agent and its thickness are mere examples, and other agents with an appropriate thickness can be used if it endures the solvent used in the following etching process. It is also possible to use another material for the etching protection layer 5 and the thickness may be changed if it endures the solvent used in the later glass plate etching process.

After the photo-resist layer 6 is fixed, as shown in FIG. 2B, the photo-resist layer 6 is exposed to reactive light through a photo-mask 7 having the pattern of the groove. In the exposure process, an aligner or a stepper used in a similar process of a normal semiconductor production can be used. After the exposure, the photo-resist layer 6 is washed by an appropriate developing agent to reveal the aperture pattern in the photo-resist layer 6.

Then the etching protection layer 5 is etched according to the aperture pattern of the photo-resist layer 6, as shown in FIG. 2C. The gold layer can be etched by a mixture of iodine, ammonium iodine, water and alcohol, and the chromium layer can be etched by a mixture of red prussiate, sodium hydroxide and water. The etching solvents exemplified here are not exhaustive but other suitable solvents can be used, of course.

Using the aperture pattern of the photo-resist layer 6 and the etching protection layer 5 as a mask, the glass plate 1 is etched by an appropriate solvent to form the groove of the flow path 8, as shown in FIG. 2D. An example of the solvent here is a 42% solution of hydrogen fluoride.

After the etching protection layer 5 and the photo-resist layer 6 are thoroughly removed, another photo-resist layer 9 is formed and is exposed through an appropriate mask to a reactive light as in the process of FIG. 2B. When the photo-resist layer 9 is etched, an aperture is formed corresponding to the mask. A reflection layer 3a is then lain over the photo-resist layer 9, as shown in FIG. 2E. The material of the reflection layer 3a is chosen so that it adequately reflects the measurement light used (i.e., ultraviolet or visible light). An example of the reflection layer 3a is an aluminum layer of less than several hundred nanometers. A protection layer 4a is further lain on the reflection layer 3a. An example of the protection layer is a sputtered quartz thin layer of tens to hundreds of nanometers.

By lifting the photo-resist layer 9, as shown in FIG. 2F, the reflection layer 3a and the protection layer 4a are patterned to cover the internal surface of the groove.

The part around the groove is then covered by a resist layer with the process similar to FIG. 2E, and the surface is covered by a low melting point glass layer of, for example, several hundred nanometers by sputtering. When the resist layer 9 is removed, the low melting point glass layer 12a is patterned as shown in FIG. 2F.

On the other glass plate 2, the other reflection layer 3b, protection layer 4b and low melting point glass layer 12b are also formed, as shown in FIGS. 2G and 2H, with a similar process as described above at FIGS. 2E and 2F.

Finally, the glass plates 1 and 2 are attached with the low melting point glass layers 12a and 12b matched, and the attached glass plates 1, 2 are put in an annealing furnace where they are heated at several hundred °C. for several hours in vacuo or in a nitrogen atmosphere. During heating, the glass plates 1 and 2 may be pressed with a force of tens to hundreds of grams. The low melting point glass layers 12a and 12b fuse in the furnace and the two glass plates 1 and 2 are thus fixed forming the flow path 8 between them, as shown in FIG. 21.

In another embodiment (second embodiment) of the present invention, another groove with the reflection layer and the protection layer may also be made in the other glass plate 2 corresponding to the first groove of the first glass plate 1. In this case, the cross section of the completed flow path 8 is elliptic, as shown in FIG. 3.

The cross section of the flow path 8 may be otherwise. When a dry etching process is used in the step of FIG. 2D utilizing $CF_4$, $C_2F_2$, $CHCF_3$ gases or a mixture thereof, the cross-section of the flow path 8 becomes near rectangular.

The material of the glass plates 1, 2 and the protection layer 4a and 4b is chosen regarding the wavelength of the measurement light 11. When, for example, a visible light is used as the measurement light, pyrex glass may be chosen. When an ultraviolet light is used, UV-22 of HOYA Corp. or #9741 of Corning Corp. can be chosen. The quartz glass cited in the above embodiment is most suited for the case using ultraviolet.

When a glass other than quartz is used as the glass plates 1 and 2, the furnace temperature for fixing the glass plates 1 and 2 should be changed accordingly. The fusing temperature of the pyrex glass is, for example, about 620° C.; that of UV-22 is about 470° C.; that of #9741 is about 600° C.; and that of quartz is about 1200° C. The temperature for fusing the two glass plates 1 and 2 must not exceed the melting point of the reflection layer. In the above embodiment, for example, since the reflection layer is made of aluminum whose melting point is about 660° C., the glass plates could not be fused by themselves because quartz is used for the glass plates. Thus the low melting point glass layer is provided between the glass plates 1 and 2 to fix them. When pyrex, UV-22 or #9741 is used, no such low melting point glass layer is necessary even if aluminum is used for the reflection layer.

Figure 4:
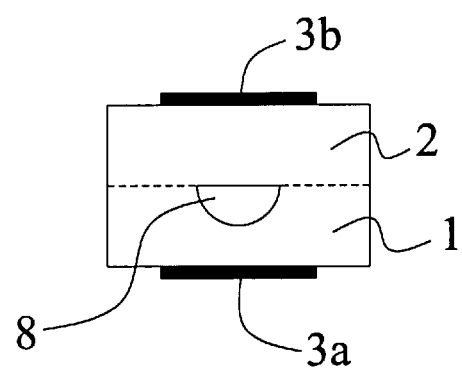
FIG. 4 is a transverse cross-sectional view of still another liquid sample cell embodying the present invention which has external reflection layers.
Figure 5:
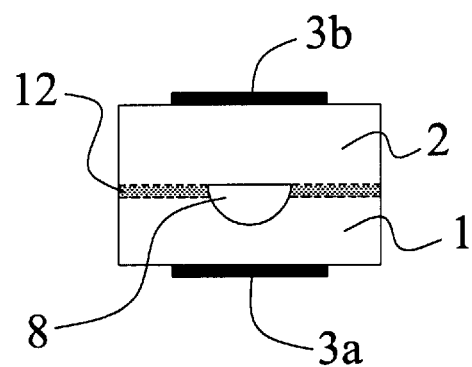
FIG. 5 is a transverse cross-sectional view of a modification to the liquid sample cell of FIG. 4 where a low melting point glass layer is used to fix the two glass plates.

As shown in FIGS. 4 and 5, the reflection layers 3a and 3b can be placed on the external surfaces of the glass plates 1 and 2. FIG. 4 shows the case where pyrex is used for the glass plates 1 and 2 so that they can be fused by themselves. FIG. 5 shows the case where quartz is used for the glass plates 1 and 2 so that they are fused with the aid of the low melting point glass layer 12. By adopting such a process that the reflection layers 3a and 3b are formed after the glass plates 1 and 2 are fused, the fusing temperature can be determined regardless of the melting point of the reflection layers 3a and 3b. In the case of FIGS. 4 and 5, the protection layer is unnecessary since the reflection layers do not contact the liquid sample. But, on the other hand, an attenuation of the measurement light should be counted since the measurement light passes through the glass plates 1 and 2 many times while it is reflected many times by the reflection layers 3a and 3b.

Figure 6:
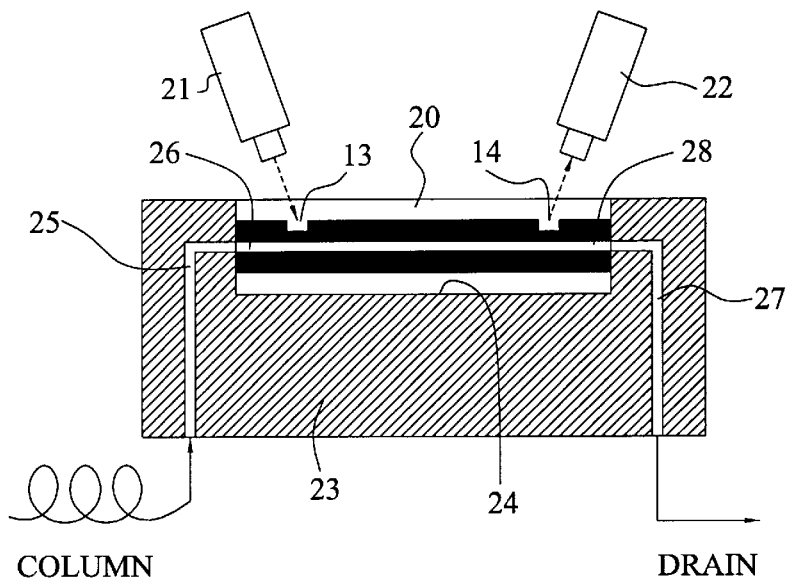
FIG. 6 is a longitudinal cross-sectional view of an example of the optical measurement apparatus according to the present invention.
Figure 7:
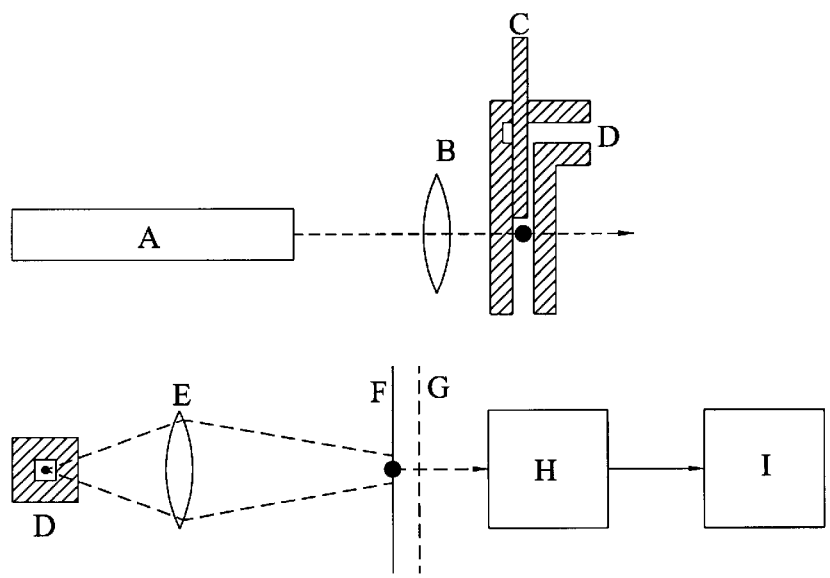
FIG. 7 is a schematic diagram of a laser excited fluorescent detector shown as a prior art optical measurement apparatus.

An optical measurement apparatus according to the present invention is shown in FIG. 6, in which: numeral 21 denotes a ultraviolet/visible light source including a deuterium lamp, a tungsten lamp and a monochromator; and 22 denotes a light detector including an optical system and a photo-detector using a photo-diode array. Both are used in ordinary ultra-violet/visible light measurements. Numeral 23 denotes a stage in which a recess 24 is provided to fix the liquid sample cell 20 as described above. When the liquid sample cell 20 is fixed in the recess 24, an entrance flow path 25 formed in the stage 23 adapts to a sample inlet 26 of the liquid sample cell 20, and an exit flow path 27 formed in the stage 23 adapts to a sample outlet 28 of the liquid sample cell 20. Further, when the liquid sample cell 20 is fixed in the recess 24, the entrance window 13 and the exit window 14 adapt to receive the measurement light from the light source 21 and give the light, after travelling a long distance in the liquid sample in the flow path of the liquid sample cell 20, out to the light detector 22. Thus a measurement can be started simply by setting the liquid sample cell 20 in the recess 24 of the stage 23.

What is claimed is:

1. A liquid sample cell used in an optical measurement apparatus in which a liquid sample flows through a flow path of the sample cell while a measurement light travels through the liquid sample in the flow path, the liquid sample cell comprising:

a first glass plate and a second glass plate fixed to each other;

the flow path being defined by a groove formed in at least one of the first glass plate and the second glass plate and an internal surface of the first glass plate or the second glass plate facing said groove;

reflection layers formed on an internal surface of the groove and on said internal surface of the first glass plate or the second glass plate; and an entrance window and an exit window formed in the reflection layers to let the measurement light into the flow path and to let the measurement light out from the flow path after the measurement light is reflected by the reflection layers a plurality of times in the flow path.

2. The liquid sample cell according to claim 1, wherein the groove is formed by a photolithographic method.

3. The liquid sample cell according to claim 1, wherein the reflection layers are made of deposited aluminum.

4. The liquid sample cell according to claim 1, wherein the reflection layers are covered by protection layers for preventing the reflection layers from contacting with the liquid sample.

5. The liquid sample cell according to claim 4, wherein the protection layers are made of quartz.

6. The liquid sample cell according to claim 1, wherein the first glass plate and the second glass plate are fixed by fusing a low melting point glass applied between them.

7. The liquid sample cell according to claim 1, wherein the first glass plate and the second glass plate are fixed by fusing the first glass plate and the second glass plate themselves at their contacting faces.

8. The liquid sample cell according to claim 1, wherein any of the first glass plate and the second glass plate whose reflection layer has the entrance window or the exit window is made of quartz.

9. The liquid sample cell according to claim 8, wherein the first glass plate and the second glass plate are fixed by fusing a low melting point glass applied between them.

10. An optical measurement apparatus comprising:

a light source for generating a measurement light;

a light detector for detecting the measurement light;

a liquid sample cell in which a liquid sample flows through a flow path of the sample cell, the liquid sample cell comprising a first glass plate and a second glass plate fixed to each other, the flow path being defined by a groove formed in at least one of the first glass plate and the second glass plate and an internal surface of the first glass plate or the second glass plate facing said groove, reflection layers formed on an internal surface of the groove and on said internal surface of the first glass plate or the second glass plate, and an entrance window and an exit window formed in the reflection layers to let the measurement light into the flow path and to let the measurement light out from the flow path after the measurement light is reflected by the reflection layers a plurality of times in the flow path; and means for fixing the liquid sample cell for letting the measurement light come in the liquid sample cell through the entrance window and for letting the measurement light enter the light detector after coming out of the liquid sample cell through the exit window when the liquid sample cell is fixed by the fixing means.

11. A liquid sample cell used in an optical measurement apparatus in which a liquid sample flows through a flow path of the sample cell while a measurement light travels through the liquid sample in the flow path, the liquid sample cell comprising:

a first glass plate and a second glass plate fixed to each other;

a groove formed in at least one of the first glass plate and the second glass plate constituting the flow path;

reflection layers formed on external surfaces of the first glass plate and the second glass plate at a place corresponding to the groove; and an entrance window and an exit window formed in the reflection layers to let the measurement light in the flow path and to let the measurement light out from the flow path after the measurement light is reflected by the reflection layers a plurality of times in the flow path.

12. The liquid sample cell according to claim 11, wherein the first glass plate and the second glass plate are made of quartz.

13. The liquid sample cell according to claim 11, wherein the groove is formed by a photolithographic method.

14. The liquid sample cell according to claim 11, wherein the reflection layers are made of deposited aluminum.

15. The liquid sample cell according to claim 11, wherein the first glass plate and the second glass plate are fixed by fusing a low melting point glass applied between them.

16. The liquid sample cell according to claim 11, wherein the first glass plate and the second glass plate are fixed by fusing the first glass plate and the second glass plate themselves at their contacting faces.

17. An optical measurement apparatus comprising:

a light source for generating a measurement light;

a light detector for detecting the measurement light;

a liquid sample cell in which a liquid sample flows through a flow path of the sample cell, the liquid sample cell comprising a first glass plate and a second glass plate fixed to each other, a groove formed in at least one of the first glass plate and the second glass plate constituting the flow path, reflection layers formed on external surfaces of the first glass plate and the second glass plate at a place corresponding to the groove, and an entrance window and an exit window formed in the reflection layers to let the measurement light in the flow path and to let the measurement light out from the flow path after the measurement light is reflected by the reflection layers a plurality of times in the flow path; and means for fixing the liquid sample cell for letting the measurement light come in the liquid sample cell through the entrance window and for letting the measurement light enter the light detector after coming out of the liquid sample cell through the exit window when the liquid sample cell is fixed by the fixing means.

* * * * *